United States Patent [19]

Steigerwald

[11] Patent Number: 4,511,357
[45] Date of Patent: Apr. 16, 1985

[54] LIQUID DRAINAGE SYSTEM WITH A GUIDABLE VALVE ELEMENT

[75] Inventor: Carl J. Steigerwald, Wauconda, Ill.

[73] Assignee: The Kendall Company, Boston, Mass.

[21] Appl. No.: 465,123

[22] Filed: Feb. 9, 1983

[51] Int. Cl.³ .............................................. A61M 1/00
[52] U.S. Cl. .................................... 604/323; 604/335; 604/350
[58] Field of Search ............................... 604/322–325, 604/335, 350; 128/760, 762, 767, 766, 205.17, 911; 137/843, 533, 533.17, 543.21, 543.19

[56] References Cited

U.S. PATENT DOCUMENTS

| | | | |
|---|---|---|---|
| 3,245,669 | 4/1966 | Huggins et al. | 137/533.17 |
| 3,586,041 | 6/1971 | Monestere | 604/323 |
| 3,965,900 | 6/1976 | Boedecker | 604/325 |
| 3,968,925 | 7/1976 | Johnston | 604/323 |
| 4,254,771 | 3/1981 | Vidal | 128/DIG. 24 |
| 4,305,404 | 12/1981 | Dunn | 128/767 |

Primary Examiner—C. Fred Rosenbaum
Assistant Examiner—J. L. Kruter
Attorney, Agent, or Firm—Powell L. Sprunger

[57] ABSTRACT

A liquid drainage system comprising, a receptacle having a chamber to receive liquid, and a depending annular wall defining a valve seat at a lower portion thereof and an opening in the region of the seat. The system has a valve element comprising a sheet of flexible relatively stiff material being sufficiently large to extend across the opening and sealingly engage against the seat peripherally around the wall. The system has a device for retaining a central portion of the valve element adjacent the seat.

15 Claims, 5 Drawing Figures

LIQUID DRAINAGE SYSTEM WITH A GUIDABLE VALVE ELEMENT

BACKGROUND OF THE INVENTION

The present invention relates to liquid drainage systems, and more particularly to urine drainage systems.

Urine drainage systems, such as urine meters, have been proposed in the past. Such systems may comprise a receptacle having a chamber, a container having a cavity, a catheter, and a drainage tube communicating between the catheter and receptacle. The catheter is passed through the urethra of a patient until a drainage eye in a distal portion of the catheter is located in the patient's bladder. During use, urine drains from the bladder through the drainage eye, the catheter, and drainage tube into the receptacle where the urine output is collected and measured.

In one form, the system may have a conduit communicating between an upper portion of the chamber and an upper portion of the cavity. When it is desirable to empty urine from the receptacle, such as when it is full, the receptacle is tilted, and the urine passes from the chamber through the conduit into the cavity for retention therein. Normally, the receptacle would be provided with a vent in an upper portion of the receptacle having a bacteria filter in order to facilitate the emptying procedure from the receptacle into the container. However, it is desirable to prevent contact of the filter by the urine when the receptacle is being emptied, since such contact may render the filter inoperable. Also, it is desirable to prevent the reflux of urine into the drainage tube, since such refluxing urine may contain bacteria which may be retrograde movement pass from the drainage tube into the bladder with possible deleterious results to the patient.

SUMMARY OF THE INVENTION

A principal feature of the present invention is the provision of an improved liquid drainage system of simplified construction.

The liquid drainage system of the present invention comprises, a receptacle having a chamber to receive liquid, and a depending annular wall defining a valve seat at a lower portion thereof and an opening in the region of the seat. The system has a valve element comprising a sheet of flexible relatively stiff material being sufficiently large to extend across the opening and sealingly engage against the seat peripherally around the wall. The system has means for retaining a central portion of the valve element adjacent the seat.

A feature of the present invention is that the valve element is in an open position spaced from the seat when the receptacle is placed in an upright position.

Thus, a feature of the present invention is that the valve element automatically permits passage of urine past the seat when the receptacle is placed in an upright position.

Still another feature of the invention is that the valve element automatically closes against the seat when the receptacle is placed in an inverted position.

Yet another feature of the invention is that the valve element closes when refluxing urine in the receptacle chamber strikes the valve element.

Thus, a feature of the present invention is that the valve element is closed against the seat when the receptacle is tilted in order to pour liquid from the receptacle chamber.

Yet another feature of the invention is that the valve element vibrates to permit passage of air from a vent on the receptacle into a lower part of the receptacle chamber when the receptacle is tilted in order to pour liquid from the receptacle chamber.

Further features will become more fully apparent in the following description of the embodiments of this invention and from the appended claims.

DESCRIPTION OF THE PREFERRED EMBODIMENTS

Figure 1:
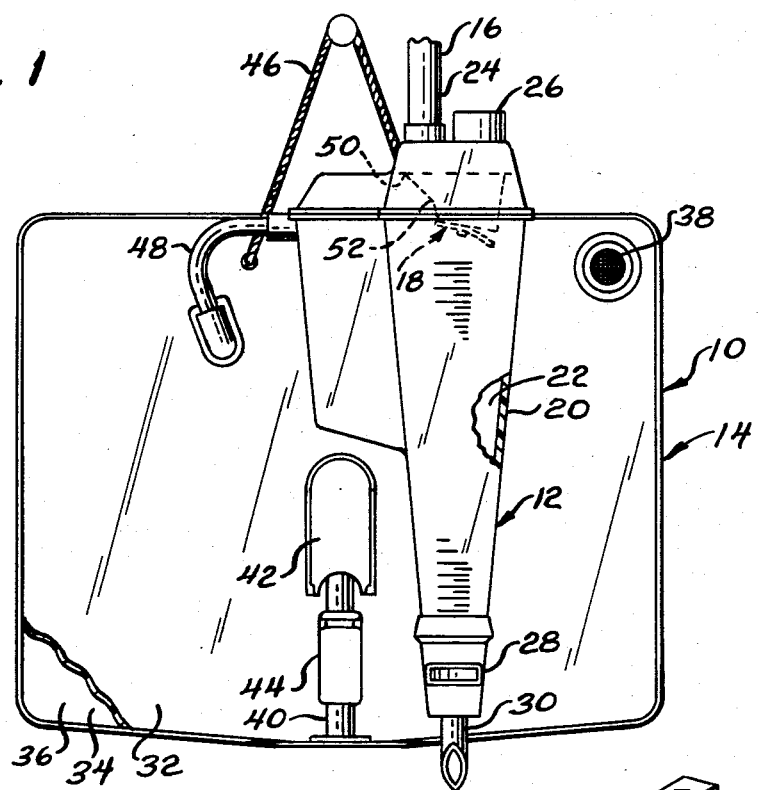
FIG. 1 is a fragmentary elevational view of a liquid drainage system of the present invention.

Referring now to FIG. 1, there is shown a liquid drainage system generally designated 10 comprising a receptacle 12, a container 14, a drainage tube 16, and a valve 18 in the receptacle 12. The receptacle 12 has a rigid outer wall 20, such as a suitable plastic material, defining a chamber 22 in the receptacle 12. As shown, a downstream end 24 of the drainage tube 16 communicates with an upper portion of the chamber 22 at a location above the valve 18. The receptacle 12 may have a vent 26 containing a bacteria filter of known type which communicates between the chamber 22 and the atmosphere in order to remove bacteria from the air passing through the vent 26 into the chamber 22. In a preferred form, as shown, the vent 26 is located above the valve 18. The receptacle 12 may also have a valve 28 of known type in order to empty urine from the chamber 22 through a tubular section 30, if it is desired to obtain a sample of the urine.

The container 14 has a front wall 32 of flexible plastic material, and a back wall 34 of flexible plastic material, with the front and back walls 32 and 34 being joined at their periphery in order to define a cavity 36 between the front and back walls 32 and 34. The container 14 may have a vent 38 having a bacteria filter of known type communicating between the cavity 36 and the atmosphere in order to remove bacteria from the air passing from the atmosphere into the cavity 36. The container 14 may have a lower tubular section 40 with an outer end received in a pocket 42 on the front wall 32 in a storage position of the tubular section 40. When it is desired to drain urine from the cavity 36, the tubular section 40 is removed from the pocket 42, and a clamp 44 of known type on the tubular section 40 is opened to permit passage of urine through the tubular section 40. After drainage of urine from the cavity 36, the clamp 44 is again closed, and the tubular section 40 is placed in the pocket 42 in the storage position of the tubular section 40. The container 14 may have a cord 46 secured to an upper portion of the container 14 in order to hang the receptacle 12 and container 14 from a suitable object, such as a bed rail, with an upper portion of the receptacle 12 being releasably retained on an upper portion of the container 14. As shown, the system 10 may have a flexible conduit 48 which communicates between an upper portion of the chamber 22 and an upper portion of the cavity 36 for a purpose which will be described below.

In use of the system 10, a catheter (not shown) is passed through the urethra of a patient until a drainage eye in a distal end of the catheter is located in the patient's bladder. In this configuration, a proximal end of the catheter located outside the patient's body is connected to an upstream portion of the drainage tube 16. Urine drains through the drainage eye, the catheter, and the drainage tube 16 into the receptacle 12 where the urine is collected and measured. When it is desired to empty urine from the receptacle 12, such as when it is full, the receptacle 12 is lifted from the container 14, and is placed in a tilted position such that the urine collects in an upper portion of the chamber 22 and passes from the chamber 22 through the conduit 48 into the container cavity 36 for retention therein. During the emptying procedure, air passes from the vent 26 through the valve 18 into a lower part of the chamber 22 to replace the liquid which passes out of the chamber 22. During this time, it is desirable to prevent the contact of urine against the bacterial filter in the vent 26, since such contacting urine may render the bacteria filter in the vent 26 inoperable. Also, it is desirable to prevent the reflux of urine from the receptacle chamber 22 into the drainage tube 16, since such refluxing urine may cause the passage of bacteria into the drainage tube 16 and by retrograde movement into the patient's bladder with possible deleterious results to the patient. Further, it is desirable to prevent the reflux of urine against the vent 26 and into the drainage tube 16 when the system 10 is mishandled, such as by turning the receptacle 12 into an inverted position. As will be seen below, the valve 18 in the receptacle 12 solves the problems associated with the prior liquid drainage systems.

Figure 2:
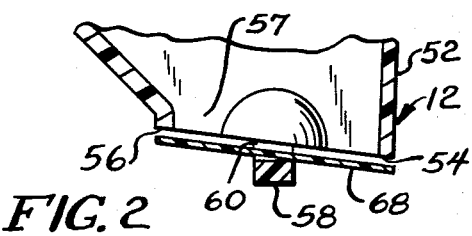
FIG. 2 is a fragmentary sectional view illustrating a valve of the system.
Figure 3:
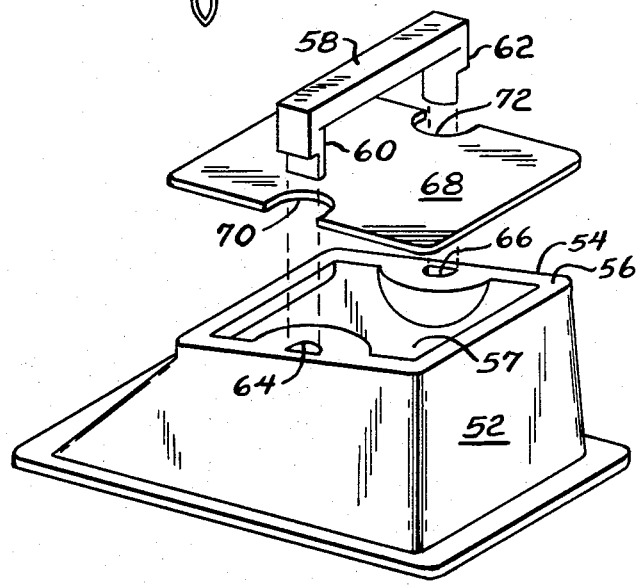
FIG. 3 is an exploded perspective view illustrating parts of the valve.

Referring to FIGS. 1-3, the receptacle 12 has a baffle 50 in an upper portion of the chamber 22, and an annular wall 52 depending from the baffle 50. The wall 52 has a rectangular lower edge 54 defining a rectangular valve seat 56 and an opening 57 in the region of the seat 56. The system 10 has an elongated retaining bar 58 with a pair of upwardly directed bosses 60 and 62 at opposed ends of the bar 58. As shown, the wall 52 has a pair of apertures 64 and 66 in the lower edge 54 in order to receive outer ends of the bosses 60 and 62. The bosses 60 and 62 may be secured in the apertures 64 and 66 by suitable means, such as by adhesive, in order to retain the bar 58 in place adjacent the valve seat 56.

The system 10 has a rectangular valve element 68 comprising a sheet of flexible relatively stiff material, such as Mylar Type A, a trademark of E. I. du Pont de Nemours of Wilmington, Del., a polyester film comprising poly(ethylene terephthalate). The valve element 68 is sufficiently large to extend across the opening 57 and sealingly engage against the seat 56 peripherally around the wall 52. A desired sheet has a tensile modulus of 555,000 p.s.i., a density of 1.395 g/cc, a tensile strength of 25,000 p.s.i., and a thickness of 5 mils. The valve element 68 has a pair of cut-outs 70 and 72 adjacent opposed sides of the valve element 68, with the bosses 60 and 62 being received in the cut-outs 70 and 72, and with the bar 58 retaining the valve element 68 in place in a central portion of the valve element 68 adjacent the valve seat 56. As shown, the valve seat 56 and valve element 68 are tilted from the horizontal when the receptacle 12 is in an upright position, with an upper portion of the valve seat 56 and the valve element 68 being located nearest the conduit 48. More specifically, and as shown in FIG. 3, valve element 68 has a pair of arcuate cut-outs 70,72 formed in the perimeter of valve element 68. Cooperating bosses 60,62 also have inner arcuate surfaces conforming to arcuate cut-outs 70,72. Thus, the bosses 60,62 and cut-outs 70,72 locate valve element 68 adjacent its seat 56 and guide the movement of valve element 68.

With reference to FIGS. 1 and 2, when the receptacle 12 is placed in an upright position the valve element 68 may assume an open position slightly spaced from the valve seat 56 in order to permit passage of urine therethrough, with the vent 26 facilitating passage of urine through the valve 18. The opening of the valve element 68 from the seat 56 is enhanced by the weight of the urine above the valve 18. When the receptacle 12 is placed in an inverted position, the valve element 68 automatically closes against the valve seat 56 due to the action of gravity on the weight of the valve element 68. Also, the reflux of urine which strikes the valve element 68 closes the valve element 68 in sealing engagement against the seat 56 in order to close the valve 18. As previously discussed, the receptacle 12 is placed in a tilted position in order to empty urine from the chamber 22 through the conduit 48 into the cavity 36. In accordance with the present invention, the valve element 68 is sufficiently flexible to vibrate and permit rapid passage of air from the vent 26 into a lower portion of the chamber 22 in order to replace the urine which passes from the chamber 22 during the emptying procedure. However, due to the stiffness of the valve element 68, the valve element 68 quickly closes after passage of air bubbles in order to prevent the reflux of urine against the vent 26 which otherwise might render the bacteria filter inoperable, and prevent the reflux of urine into the drainage tube 16 which may permit bacteria by retrograde movement to pass into the patient's bladder with possible deleterious results to the patient.

Figure 4:
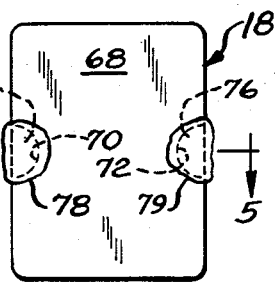
FIG. 4 is a lower plan view of another embodiment of the valve of the present invention.
Figure 5:
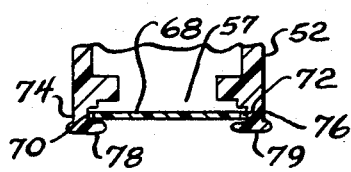
FIG. 5 is a fragmentary sectional view taken substantially as indicated along the line 5—5 of FIG. 4.

Another embodiment of the valve 18 of the present invention is illustrated in FIGS. 4 and 5, in which like reference numerals designate like parts. In this embodiment, the wall 52 has a pair of pins 74 and 76 depending from the wall 52 at opposed sides of the valve element 68, with the pins 74 and 76 having enlarged outer ends 78 and 79. As before, the valve element 68 has a pair of cut-outs 70 and 72 adjacent opposed sides of the valve element 68, and the pins 74 and 76 are received in the cut-outs 70 and 72 to retain the valve element 68 in place adjacent the valve seat 56. In this manner, a central portion of the valve element 68 is retained adjacent the valve seat 56. In other respects, the valve 18 of FIGS. 4 and 5 operates in a manner similar to that previously described in connection with the valve of FIGS. 1-3. More specifically and as shown in FIGS. 4-5, pins 74,76 define boss member means, each having an inner arcuate surface conforming to the arcuate cut-outs 70,72 formed in the perimeter of valve element 68. Thus, the pins 74,76 with their inner arcuate surfaces and the cut-outs 70,72 locate valve element 68 adjacent its seat 56 (FIGS. 2-3) and guide the movement of valve element 68. The enlarged outer ends 78,79 on pins 74,76 restrain movement of valve element 68.

The foregoing detailed description is given for clearness of understanding only, and no unnecessary limitations should be understood therefrom, as modifications will be obvious to those skilled in the art.

I claim:

1. A urine drainage system, comprising:

a receptacle having a chamber to receive urine, and a depending annular wall defining a valve seat at a lower portion thereof and an opening in the region of the seat;

a valve element comprising a sheet of flexible relatively stiff material being sufficiently large to extend across said opening and sealingly engage against said seat peripherally around the wall; and means for retaining a central portion of the valve element adjacent to the seat comprising a generally straight bar extending completely across a central portion of the valve element and having a pair of boss member means adjacent opposed ends of the bar, said boss member means being secured to the receptacle wall, the valve element having a pair of arcuate cut-outs along the perimeter to coincide with the boss member means, the boss member means having an inner arcuate surface to conform to the arcuate cut-outs on the perimeter of the valve element to locate the valve element adjacent the valve seat and guide the movement of the valve element.

2. The system of claim 1 wherein said valve element and seat are generally rectangular.

3. The system of claim 1 wherein said valve element comprises a polyester film.

4. The system of claim 1 including a vent communicating between the atmosphere and the valve element at a location above the valve element when the receptacle is in an upright position.

5. The system of claim 1 including a drainage tube communicating with the chamber at a location above the valve element when the receptacle is located in an upright position.

6. The system of claim 1 including a container having a cavity.

7. The system of claim 6 including a conduit communicating between an upper portion of the chamber and an upper portion of the cavity.

8. The system of claim 7 wherein said valve element and seat are tilted from the horizontal with an upper portion of the valve element and seat being located nearest the conduit.

9. The system of claim 1 wherein the wall extends from a baffle located in an upper portion of the chamber.

10. The system of claim 1 wherein the valve element comprises poly(ethylene terephthalate).

11. The system of claim 1 wherein the valve element has a tensile modulus of approximately 555,000 p.s.i.

12. The system of claim 1 wherein the valve element has a density of approximately 1.395 g/cc.

13. The system of claim 1 wherein the valve element has a tensile strength of approximately 25,000 p.s.i.

14. The system of claim 1 wherein the valve element has a thickness of approximately 5 mils.

15. A urine drainage system, comprising:

a receptacle having a chamber to receive urine, and a depending annular wall defining a valve seat at a lower portion thereof and an opening in the region of the seat;

a valve element comprising a sheet of flexible relatively stiff material being sufficiently large to extend across said opening and sealingly engage against said seat peripherally around the wall; and means for retaining a central portion of the valve element adjacent to the seat comprising a pair of pins defining boss member means, the valve element having a pair of arcuate cut-outs along the perimeter to coincide with the boss member means, the boss member means having an inner arcuate surface to conform to the arcuate cut-outs on the perimeter of the valve element to locate the valve element adjacent the valve seat and guide the movement of the valve element, the pins further having enlarged outer ends to restrain the movement of the valve element.

* * * * *